(12) United States Patent
Baer et al.

(10) Patent No.: US 6,493,417 B1
(45) Date of Patent: Dec. 10, 2002

(54) PATIENT POSITIONING FOR CONDUCTING A MEDICAL EXAMINATION

(75) Inventors: Ulrich Baer, Neunkirchen (DE); Martin Schmidt, Emskirchen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/718,061

(22) Filed: Nov. 21, 2000

(30) Foreign Application Priority Data

Nov. 23, 1999 (DE) .......................................... 199 56 268
Oct. 20, 2000 (DE) .......................................... 100 52 193

(51) Int. Cl.$^7$ ................................................ A61B 6/04

(52) U.S. Cl. ........................ 378/20; 378/208; 378/209; 5/601

(58) Field of Search ............................ 378/18, 20, 163, 378/195, 207, 208, 209; 5/600, 601, 611

(56) References Cited

U.S. PATENT DOCUMENTS

| | | | | |
|---|---|---|---|---|
| 3,585,386 A | * | 6/1971 | Horton | ........................ 250/50 |
| 4,067,565 A | * | 1/1978 | Daniels | ......................... 5/601 |
| 4,233,507 A | | 11/1980 | Volz | |
| 4,651,335 A | | 3/1987 | Kalender et al. | |
| 4,870,666 A | | 9/1989 | Lonn et al. | |
| 4,893,323 A | * | 1/1990 | Cook, III | .................... 378/208 |
| 5,226,070 A | * | 7/1993 | Ariba et al. | ................ 378/208 |
| 5,365,565 A | * | 11/1994 | Barbaric | ...................... 378/146 |
| 5,841,835 A | * | 11/1998 | Aufrichtig et al. | .......... 378/207 |

* cited by examiner

Primary Examiner—David P. Porta
Assistant Examiner—Therese Barber
(74) Attorney, Agent, or Firm—Schiff Hardin & Waite

(57) ABSTRACT

A positioning arrangement has a positioning element formed of a closed-cell foam, preferably a positioning mat, the positioning element has a seating surface for an examination subject to be examined with computed tomography and has an underside provided with a recess into which a reference member can be introduced. The recess has a holder for the reference member that holds the reference member introduced into the recess with a positive fit in a defined position relative to the seating surface.

12 Claims, 2 Drawing Sheets

PATIENT POSITIONING FOR CONDUCTING A MEDICAL EXAMINATION

BACKGROUND OF THE INVENTION

1. Field of the Invention

The present invention is directed to a positioning arrangement of the type having a seating surface for an examination subject to be examined in a computed tomography apparatus, and which has a recess into which a reference member can be introduced.

2. Description of the Prior Art

Such positioning arrangements are employed for the implementation of osteo-examinations wherein the aim is to determine the density values of the bone material of a patient on the basis of a reference member formed of a defined material. For these examinations, the reference member must assume a defined position relative to the patient; namely, it must be positioned relative to the longitudinal axis of the patient so that it produces an image in the examination of a diagnostically relevant region of the patient. Second, it must exhibit a defined spacing from the body surface of the patient.

In this context, U.S. Pat. No. 4,233,507 discloses that reference members be fixed in a positioning plate serving for the positioning of the patient. It is difficult if not impossible to replace reference members in this case. This publication also discloses that reference members be arranged in a removable part of the positioning plate.

U.S. Pat. No. 4,651,335 discloses the use of a positioning pillow or cushion containing reference members, these being arranged between the patient and a positioning plate serving for the positioning of the patient. It is difficult to assure an exact positioning of the reference members relative to the patient in this case.

U. S. Pat. No. 4,870,666 discloses a positioning means of the type initially described that is fashioned as a cushion that can be placed on a positioning plate, the upper side of the positioning plate being provided with a recess for the acceptance of reference members.

A positioning mat that can be placed on a positioning plate is also known that has a receptacle that is covered with a glued-on foil at the underside of the positioning plate. The reference members are placed into this receptacle proceeding from above, i.e. proceeding from the seating surface of the positioning mat.

Additional cushions or spacers of expanded cellular material are required with this positioning mat in order to be able to correctly position the reference member relative to the patient; one cushion maintains the correct position of the reference member in the direction of the longitudinal axis of the patient, and another cushion assures the correct spacing of the reference member from the body surface of the patient.

This known arrangement also has a number of serious disadvantages. The clearance for the reference member is open toward the patient, so that body fluids can penetrate, these being difficult to remove. In particular, the corners cannot be disinfected in a satisfactory manner. The reference body, which is freely exposed at the top, presses against the patient's back. Additional cushions of expanded cellular material are required in order to position the reference member in the correct position relative to the patient, these being easily lost in routine clinical work. During storage, the reference member easily falls out of the positioning mat. Lastly, the glued location between positioning mat and foil frequently tears.

SUMMARY OF THE INVENTION

An object of the present invention is to provide a positioning arrangement of the type initially described which can be dependably handled.

This object is inventively achieved in a positioning arrangement having a positioning element seating surface for an examination subject to be examined in a computed tomography procedure, this positioning procedure being provided with a recess at its underside into which a reference member can be introduced.

The seating surface can be smooth since, in the inventive positioning arrangement, the recess (preferably adapted in shape to the reference member) is provided at the underside of the positioning means facing away from the seating surface. Differing from known positioners, no contaminants can collect in the mounting region for the reference member. Contaminants can be easily removed and it is easy to disinfect the seating surface.

In a preferred embodiment of the invention, the recess has a holder for the reference body that places the reference body introduced into the recess into a defined position relative to the seating surface. The correct position of the reference body relative to the seating surface, and thus relative to the patient is assured by the recess being adapted in shape to the reference member and being provided with this holder, without requiring additional cushions of expanded cellular material for the correct positioning of the reference member.

In one version of the invention, the reference member is held with a positive fit in the recess, so that the reference member can remain in the recess when the positioning arrangement is in storage. It is thus assured that the reference is always present when the positioning arrangement is employed and cannot be lost.

In an embodiment of the press fit, the reference member can be introduced into the recess with plastic deformation of the positioning element, so that it can in turn be removed asa needed, for example in order to replace it with a different reference member.

All materials that exhibit an adequately low X-ray absorption and do not promote the formation of artifacts in the images are suitable as material for the positioning arrangement. The formation of the positioning arrangement as a mat composed of a closed-cell foam, for example PE foam as distributed under the name EVAZOTE 50, is preferred.

The reference member preferably has an oblong shape and the recess is disposed in the positioning element so that the longitudinal axis of the reference member proceeds substantially parallel to the longitudinal axis of the positioning element. Given human patients, a parallel attitude of the reference member relative to the spinal column is then established.

In order to make the position of the reference member visible, and thus facilitate its relative position to the region of the patient that is to be simultaneously scanned with the reference member, the seating surface—in one version of the invention—is provided the markings indicating the axial position of the reference member. These markings are preferably fashioned such that they do not tend to become contaminated and are easy to clean.

The positioning arrangement is preferably provided as an overlay for a positioning plate and can be provided with fasteners, for example Velcro® bands, for fastening to the positioning plate.

In an especially preferred embodiment of the invention, the positioning arrangement is displaceable in the direction of the longitudinal axis relative to the positioning plate in order to be able to adapt the position of the reference member to different patient sizes.

When the positioning arrangement is provided as an overlay for a positioning plate, in a version of the invention the positioning arrangement is provided with at least one oblong projection that overlaps a limiting edge of the positioning plate. A contamination of the positioning plate is thus largely prevented. Repositioning of the patient is facilitated when the material of the positioning means is resilient, since this avoids the patient having to be transported over a hard edge of the positioning plate.

DESCRIPTION OF THE PREFERRED EMBODIMENTS

Figure 1:
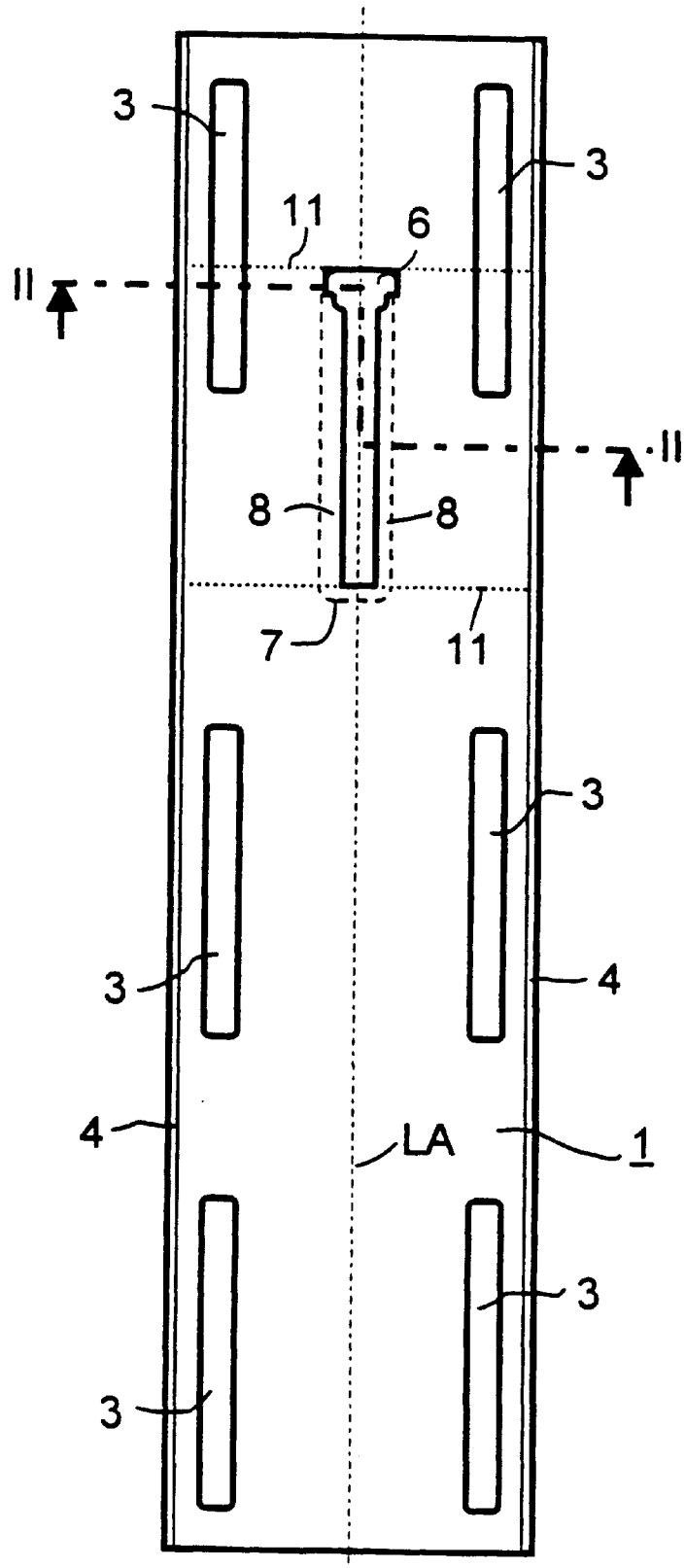
FIG. 1 is a view of the underside of an inventive positioning arrangement.

As can be seen from FIG. 1, the inventive positioning arrangement includes a positioning element 1 that is fashioned symmetrical relative to its longitudinal axis, which is referenced LA. The positioning element 1 is in the form of a mat manufactured of a closed-cell, elastically deformable expanded material, preferably a PE foam obtainable under the name "EVAZOTE 50", and—as can be seen from FIG. 2—is fashioned as an overlay for the positioning plate 2 of a CT apparatus that is otherwise not shown. As used herein "a mat" means a planar, flexible structure that yields to pressure in the sense of a cushioning.

In order to assure a secure positioning of an examination subject, for example a patient, the positioning element 1 as well as the positioning plate 2 are fashioned slightly concave.

Schematically indicated Velcro® connections 3 are provided for fastening the positioning element to the positioning plate 2. These connections 3 extend in the direction of the longitudinal axis LA over a large part of the length of the positioning element 1 and the positioning plate 2 and thus also assure a secure hold of the positioning element 1 on the positioning plate 2 when the positioning element 1 is displaced on the positioning plate 2 in the direction of the longitudinal axis LA.

At each of its two edges proceeding parallel to the longitudinal axis LA, the positioning element 1 has a projection 4 extending along the entire length of the positioning element 1. This projection 4 overlaps the corresponding limiting edge 5 of the positioning plate 2, so that a guidance of the positioning element 1 relative to the positioning plate 2 is assured and the penetration of dirt between the underside of the positioning element 1 and the positioning plate 2 also is prevented.

The inventive positioning element 1 is provided for the implementation of osteo-examinations and therefore inventively accepts an oblong reference member 6 in a recess 7, such that the longitudinal axis of the reference member 6 proceeds substantially parallel to the longitudinal axis LA of the positioning plate 2. The recess 7 is provided in the underside of the positioning element 1 facing toward the positioning plate 2. The underside of the positioning element 1 faces away from the seating surface 9 of the positioning element 1 that accepts a patient during the implementation of the osteo-examination. For the implementation of an osteo-examination, the positioning element 1 replaces a similar positioning means used for other examinations that does not have a reference member nor a corresponding recess.

The reference member 6, which is introducible into the recess 7 by elastic deformation of the positioning element 1, is held with positive fit in the recess 7 by a holder 8. In order to assure that the reference member 6 assumes a defined position relative to the positioning surface 9 of the positioning element 1 that accepts the patient during the implementation of the osteo-examination, the recess 7 is adapted in shape to the reference member 6, i.e. is shaped such that the reference member 6 cannot be displaced to a noteworthy extent in the recess 7 either in the direction of the longitudinal axis LA or transversely relative thereto. The holder 8 also assures that the reference member 6 cannot fall out of the recess 7 and simultaneously seats the reference member against the base surface 12 of the recess 7.

The holder 8 is in the form of ledge-like projections applied to the longitudinal edges of the recess 7, the length of those projections—as can be seen from FIG. 1—being less than the length of the recess 7, so that an area in which the holder 8 does not produce a cross-sectional constriction of the recess 7 exists at the one end of the recess.

Figure 2:
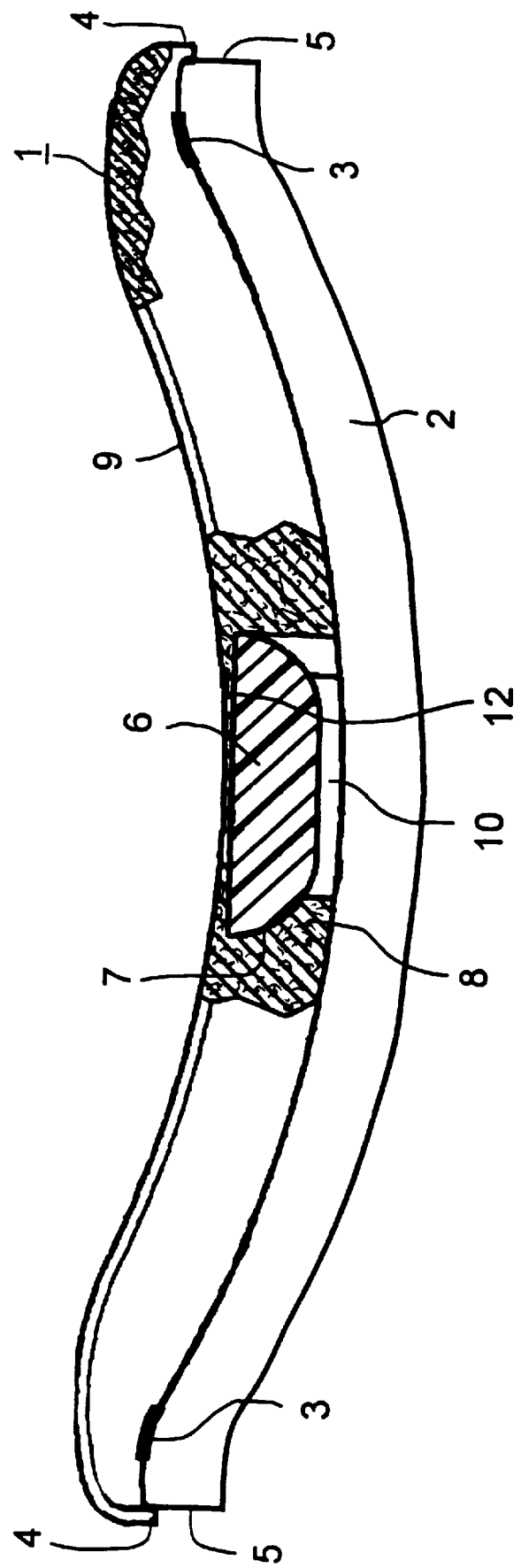
FIG. 2 is a sectional view along the line II—II in FIG. 1.

The projections are thus recessed at the one face side of the recess 7, so that it is possible—at this end face—to introduce the one end of the reference member 6 into that region of the recess 7 without cross-sectional constriction, and then, given elastic deformation of the positioning element 1, to push it completely into the recess 7, whereby the holding means 8 and the reference member 6 engage in the fashion of a dovetail-like guide, as can be seen from FIG. 2.

The recess 7 is fashioned to produce a spacing of the reference member 6 from the seating surface 9, as well as to produce defined spacing of the reference member 6 from the positioning plate 2 as air gap 10.

The air gap 10 is provided in order to make it possible for a software program of the CT apparatus to automatically find the contours of the reference member 6 in a CT image.

In the described exemplary embodiment, the reference member 6 has two plane-parallel limiting surfaces of different width, whereby the broader surface lies against the base surface 12 of the recess 7 and thus faces toward the seating surface 9 and the narrower surface faces toward the positioning plate 2. The two plane-parallel surfaces are connected by convex, circularly curved lateral surfaces. These lateral surfaces can be curved, for example, according to a quarter-circle in cross-section.

The seating surface 9 is provided with marks 11 proceeding transversely relative to the longitudinal axis LA that are indicated as dotted cross lines in FIG. 1, which shows that side of the positioning element 1 that faces toward the positioning plate 2 during use. These marks 11 indicate to the medical personnel the region in which the reference member 6 (which is not visible as a result of being attached to the underside of the positioning element 1) is situated. The medical personnel are thus able to place the patient on the positioning element 1 so that the reference member 6 is imaged in common with the diagnostically relevant region of the patient.

The design of the positioning element 1, the reference member 6, the recess 7 as well as the guides 9 in the above-described exemplary embodiment should be understood only as an example. This is also true of the fashioning of the positioning element as a mat that can be placed on a positioning plate. The important feature of the invention is that the reference member 6 is accepted in a recess 7 provided at the underside of the positioning element and is held in a defined position relative to the seating surface therein by a holder.

Although modifications and changes may be suggested by those skilled in the art, it is the intention of the inventors to embody within the patent warranted hereon all changes and modifications as reasonably and properly come within the scope of their contribution to the art.

We claim as our invention:

1. A positioning arrangement for conducting a medical examination, comprising:

positioning element having a seating surface adapted to receive an examination subject; and said positioning element having an underside with a recess therein facing away from said seating surface adapted to receive a reference member for use in computed tomography.

2. A positioning arrangement as claimed in claim 1 further comprising a holder in said recess adapted to bring and maintain said reference member, when in said recess, in a defined position relative to said seating surface.

3. A positioning arrangement as claimed in claim 2 wherein said holder is adapted to hold said reference member in said recess with a positive fit.

4. A positioning arrangement as claimed in claim 2 wherein said positioning element, at least surrounding said recess, is elastically deformable to allow introduction in said reference member into said recess.

5. A positioning arrangement as claimed in claim 1 wherein said recess is adapted to receive a reference member having an oblong shape with a longitudinal axis, and wherein said recess is disposed in said positioning element so that when said reference member is in said recess, said longitudinal axis of said reference member is substantially parallel to a longitudinal axis of said positioning element.

6. A positioning arrangement as claimed in claim 5 wherein said seating surface has markings therein indicating an axial position of said reference member.

7. A positioning arrangement as claimed in claim 1 formed as an overlay for a positioning plate.

8. A positioning arrangement as claimed in claim 7 wherein said positioning element is a positioning mat.

9. A positioning arrangement as claimed in claim 7 further comprising fasteners adapted for fastening said positioning element to said positioning plate.

10. A positioning arrangement as claimed in claim 7 wherein said positioning element has at least one oblong projection adapted to overlap a limiting edge of said positioning plate.

11. A positioning arrangement as claimed in claim 7 wherein said recess has a depth so that an air gap is produced between said reference member and said positioning plate when said reference member is in said recess.

12. A positioning arrangement as claimed in claim 1 wherein said positioning element is comprised of a closed-cell foam.

\* \* \* \* \*